United States Patent [19]

Kindel et al.

[11] 4,221,146

[45] Sep. 9, 1980

[54] TROUGH TO BE USED IN A MICROTOME OR AN ULTRAMICROTOME

[75] Inventors: Lennart Kindel, Älvsjö, Sweden; William S. Mansfield, Cambridge, England

[73] Assignee: LKB-Produkter AB, Bromma, Sweden

[21] Appl. No.: 939,235

[22] Filed: Sep. 5, 1978

[30] Foreign Application Priority Data

Sep. 5, 1977 [SE] Sweden ............................... 7709931

[51] Int. Cl.² ............................................. G01N 1/06
[52] U.S. Cl. .................................. 83/167; 83/915.5; 83/651
[58] Field of Search ....................... 83/915.5, 167, 651

[56] References Cited

U.S. PATENT DOCUMENTS 3,225,639  12/1965  Martinelli ........................... 83/915.5

OTHER PUBLICATIONS

An Ultramicrotome Knife Trough for Glass Knives, John H. Wyatt, Journal of Electron Microscopy, vol. 21, No. 1, 89-90 (1972).

Primary Examiner—Donald R. Schran
Attorney, Agent, or Firm—Fisher, Christen & Sabol

[57] ABSTRACT

A triangular trough for collecting specimens from the knife edge of a microtome, or ultramicrotome is made of a form cast plastic material, one of the side walls projecting downwardly below the bottom wall of the trough to allow the trough to be adhesively attached to the side of the knife. The trough is inexpensive enough to be suitable for one time use.

3 Claims, 4 Drawing Figures

U.S. Patent  Sep. 9, 1980  4,221,146
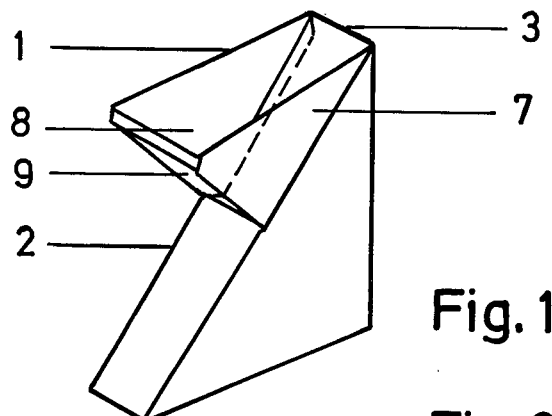
Fig. 1
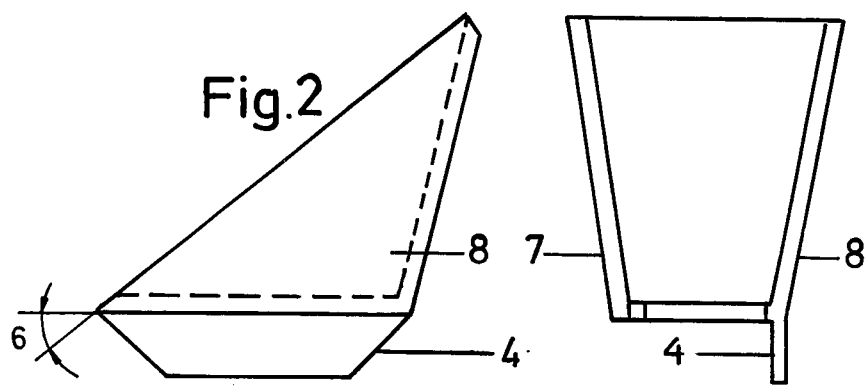
Fig. 2
Fig. 3
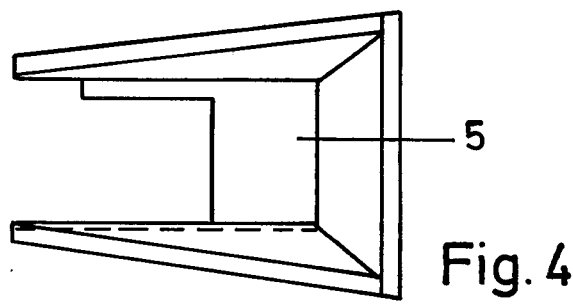
Fig. 4

TROUGH TO BE USED IN A MICROTOME OR AN ULTRAMICROTOME

The present invention refers to a trough to be filled with liquid and to be used for collecting sample sections which are cut in a microtome or an ultramicrotome from a specimen block by making the block pass a knife with an horizontal edge behind which the knife has a sloping rectangular surface.

The specimen sections produced in microtomes and especially in ultramicrotomes for further investigation in light microscopes or electron microscopes respectively are too thin to be handled directly with a pair of forceps or other handtools. Usually the section producing knife is therefore provided with a liquid surface on which the sections are made to float and from which they are collected by means of a sample carrier net or some similar means. This liquid surface is thereby obtained by filling a trough arranged behind the knife edge with liquid, the trough usually being arranged directly on the knife which in ultramicrotomes usually is a triangular vertical glass plate, the upper horizontal edge of which is used as a knife edge. Behind the knife edge is thereby obtained a sloping rectangular surface and the trough is usually obtained by adapting an adhesive tape around this surface. The sealing towards the glass is thereby obtained with the adhesive material on the tape or could be obtained by using melted wax or nailpolish. Metal troughs obtained from U-formed metal bands are also sometimes used.

Both the above mentioned types of troughs do however have essential drawbacks. The use of tape troughs requires a high skill in order to adapt the troughs in a correct way and the procedure is very time consuming. In using tape troughs it's thus difficult to obtain a satisfactory sealing and furthermore the troughs easily obtain an unsuitable shape. The liquid surface shall namely give a big reflecting surface in order to make the sections floating thereon visible. If the tape is not sufficiently stretched around the knife the reflecting surface will be limited to certain spots and the work with the section will be difficult. Furthermore one easily obtains contamination of the liquid in the trough which affects the subsequent evaluation of the sections in the microscope. Also the metal troughs, which are used to a smaller extent, have essential drawbacks which among other thing consist therein that the troughs because of their high heat capacity have to be preheated over an open flame in order to make the sealing medium, usually wax, seal in a sufficient way. Furthermore the stiff metal troughs are difficult to apply on knifes with different widths. Furthermore the metal troughs are too expensive to be applied for one time use and thus to have to be cleaned between subsequent uses which is time consuming and furthermore involves a risk of contamination.

It is an object of the present invention to provide a trough in which the above discussed drawbacks are eliminated. The characteristics of the trough thereby appear from the claims attached to the specification.

The trough according to the invention will now be described in detail reference being made to the enclosed drawing in which;

FIG. 1 shows a perspective view of a trough according to the invention applied on a knife and FIG. 2 is a view from the rear of FIG. 1 with the trough tilted to the left;

FIG. 3 is a view of the trough alone from the right in FIG. 1, and

FIG. 4 is a view from the top.

In FIG. 1 reference 1 denotes a trough according to the invention which is applied on a glassknife 2 consisting on a triangular glass plate, the upper horizontal edge 3 of which constitutes the knife edge. The trough 1, which is suitably made from a formcast piece of plastic consists of two sidewalls 7 and 8 respectively and rear wall 9. Furthermore the trough is provided with a bottom 5 in order to provide a bigger contact surface between the trough and the knife. According to the invention the trough is furthermore provided with a vertical flange 4 to be brought in contact with one vertical side of the glassknife 2. The flange 4 guides the trough when applied to the knife irrespectively of the length of the edge of the knife. When applying the trough, the innerwall of the flange and the outer surface of the bottom 5 are provided with a floating wax or similar sealing means. The trough could then be displaced to a desired position so that the upperedge of the trough will be brought on the same level as the knife edge 3 before the wax has become solid. This allows a perfect orientation. In order to obtain an optimum liquid reflection the choice of the angle 6 is thereby of the outmost importance. This angle is thereby adapted to the position of the glassknife at cutting so that the upper edge of the trough at the cutting will be substantially horizontal. As the trough is suitably made in form cast plastic the price will be so low as to permit one time use of the trough. Furthermore the plastic material has such a low heat capacity that the trough does not have to be preheated but the melted wax could be applied directly on the trough.

We claim:

1. In a disposable trough fabricated from a material having low heat-conductivity to be adhesively attached to the knife of a microtome or ultramicrotome to provide a body of liquid for collecting samples as they are sectioned by said knife, said knife having a generally sloping surface intersected by at least one generally vertical side surface extending downwardly from one side of the sloping surface, the improvement which comprises:
   two horizontally spaced generally triangular sidewalls, the upper margins thereof to be disposed generally in a horizontal plane;
   a third wall connected between said sidewalls adjacent a respective one of the remaining margins of each sidewall;
   the other remaining margin of one of the sidewalls and the lower margin of the third wall to be in contact with said sloping surface of the knife;
   the other of the sidewalls being provided with a depending flange defining the other remaining margin of the other sidewall;
   said depending flange to be placed in abutment against said side surface of the knife;
   whereby said trough when in position defines with the sloping surface of the knife an open vessel for liquid for collecting said sectioned sampled.

2. A trough as defined in claim 1, wherein the lower margins of said third wall and said one sidewall are defined by a narrow surface parallel with said sloping surface to maximize the surface contact between said margins and the sloping surface.

3. A trough as defined in claim 1, wherein a bottom wall to be disposed in surface contact with said sloping surface extends between said sidewalls.

* * * * *